United States Patent [19]

Leonard

[11] 4,104,799

[45] Aug. 8, 1978

[54] DENTAL HANDPIECE

[75] Inventor: Henri Leonard, Besancon, France

[73] Assignee: Micro-Mega S.A., France

[21] Appl. No.: 751,999

[22] Filed: Dec. 17, 1976

[30] Foreign Application Priority Data

Dec. 22, 1975 [FR] France .................. 75 39915
Oct. 20, 1976 [FR] France .................. 76 32151

[51] Int. Cl.² ........................................ A61C 1/08
[52] U.S. Cl. ............................................. 32/26
[58] Field of Search ............... 279/71, 72, 75, 22; 32/26, 27

[56] References Cited

U.S. PATENT DOCUMENTS 3,070,380  12/1962  Holmberg ................. 279/75
3,631,597  1/1972  Lieb ........................ 32/26
3,803,716  4/1974  Garnier ................... 32/26

Primary Examiner—Robert Peshock
Attorney, Agent, or Firm—Robert E. Burns; Emmanuel J. Lobato; Bruce L. Adams

[57] ABSTRACT

An axially slidable chuck-actuating internal sleeve of a dental handpiece is biased to a chuck-closing position by a spring, but can be displaced to open the chuck by cooperation with radially-movable balls. These balls are biased outwardly by leaf springs to normally rest in contact with the inner surface of an axially slidable or rotatable external actuating sleeve, whereby the balls remain out of contact with the internal sleeve when it is rotated with the handpiece shaft.

9 Claims, 4 Drawing Figures

4,104,799

DENTAL HANDPIECE

BACKGROUND OF THE INVENTION

The invention relates to dental handpiece of the type comprising a hollow body, a central rotary shaft rotatably mounted in the body, a tool-gripping chuck carried by a forward end of the shaft, a first chuck-actuating sleeve slidably axially mounted on the shaft between a first position corresponding to a tool-gripping position of the chuck and a second position corresponding to a tool-release position of the chuck, a spring biasing the gripping sleeve axially relative to the shaft, at least one radially-movable ball cooperating with a generally conical wall of the first sleeve, and an external second chuck-actuating sleeve on the body cooperating with the ball to radially inwardly move the ball to axially move the first sleeve against the action of the biasing spring.

In known handpieces of this type, the chuck is held in a tool-gripping position by pressing the balls inwardly against the generally conical wall of the first sleeve, and holding the balls in this position by an inner fixing cone. When the central shaft rotates, the first sleeve also rotates together with the balls and the fixing cone, so that it is necessary to carefully balance the parts. Also, the fixing cone is coupled with the external second actuating sleeve by an arrangement designed to reduce friction between these two parts. For example, the second sleeve is connected to the fixing cone by a sliding piece and two guide pieces, the sliding piece being lodged in a groove in the fixing cone. However, there is still a risk of friction being set up between the sliding piece and the fixing cone when the latter is rotated.

An aim of the invention is to avoid the aforementioned disadvantages, and particularly to eliminate any friction between the parts of the chuck actuating device when the handpiece shaft is rotated.

SUMMARY OF THE INVENTION

According to the invention, in a handpiece of the aforementioned type said at least one ball is disposed in an opening of the body, a second spring biasing said ball radially outwardly to a rest position against an inner wall of the second sleeve and out of contact with said conical wall of the first sleeve, in which rest position of the ball the first sleeve is biased by the first biasing spring to said first position, the second sleeve being manually movable and having on its inner wall an inclined part which moves the ball radially inwardly against the action of the second spring through said opening and into contact with said conical wall of the first sleeve to move the first sleeve to its second position in response to movement of the second sleeve.

Hence, since the balls and their actuating means remain out of contact with the rotary parts when the chuck is in the tool-gripping position, the friction problem is avoided and the new arrangement enables the second sleeve to directly act as actuating member for the balls, thus eliminating the separate fixing cone of the previous arrangements.

BRIEF DESCRIPTION OF THE DRAWINGS

Two embodiments of the invention will be described, by way of example, with reference to the accompanying drawings, in which:

FIG. 1a is a perspective view of a spring for biasing the ball;

DESCRIPTION OF THE PREFERRED EMBODIMENTS

Figure 1:
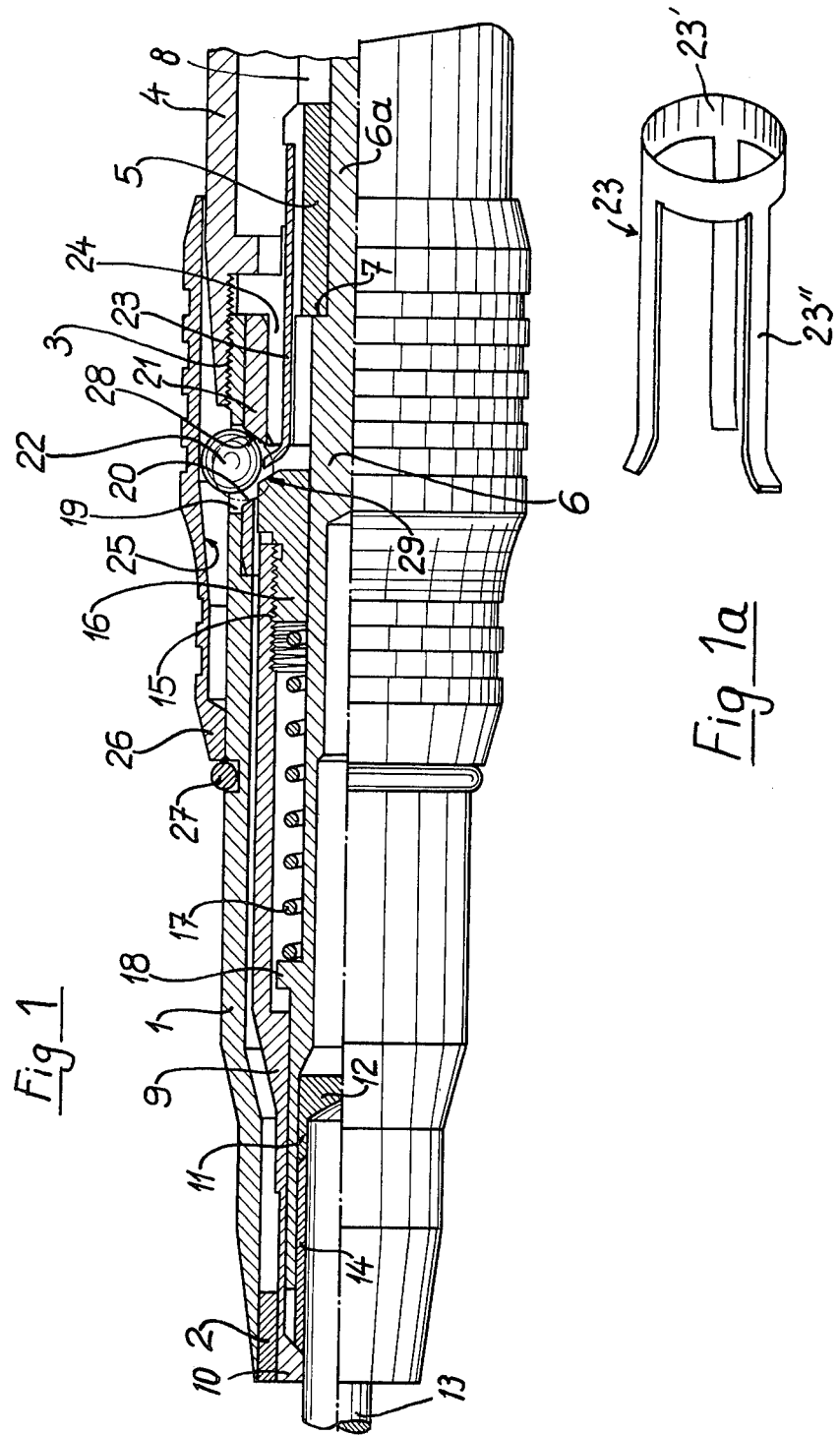
FIG. 1 shows the first embodiment of handpiece according to the invention, partially in cross-section.
Figure 2:
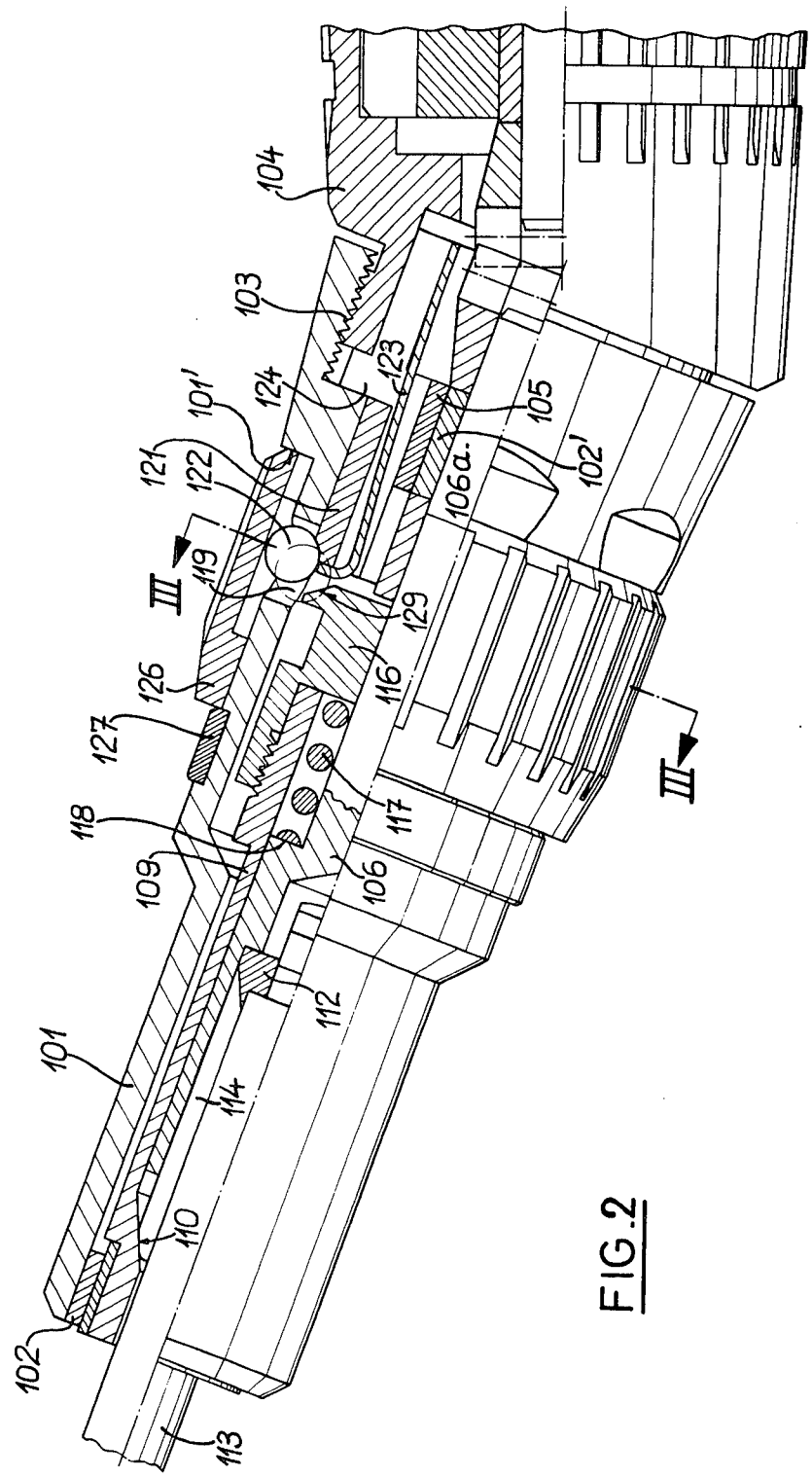
FIG. 2 shows the second embodiment of handpiece partly in cross-section.

With reference to FIGS. 1 and 2, a dental handpiece is composed of a principal body 1 provided at the front end with a bearing 2 and at the rear end with an external threading 3 on which is screwed a rear sleeve 4 by which the handpiece is fitted on a motor or a wrist joint. A bearing 5 clamped inside the sleeve 4 at the rear of the principal body 1 supports a rear end 6a of reduced diameter of a central shaft 6 which is secured to the driving element by a driving piece 8. A shoulder 7 of bearing 5 cooperates with a shoulder of shaft 6 to limit its play.

On the forward end of shaft 6 is mounted a clamping sleeve 9. The forward end of sleeve 9 has a flange 10 with an internal conical edge which forms one of the elements of the tool-clamping chuck. The second element of the chuck is formed by an internal conical edge of a sleeve 11 on a hollow piece 12 force-fitted in the bored forward end of the shaft 6, the piece 12 serving as an abutment for the fitted tool 13. Clamping pincers 14 whose ends have conical surfaces are confined between the corresponding conical edge of the flange 10 of clamping sleeve 9 and the sleeve 11 of piece 12.

The forward end of the clamping sleeve 9 is supported in the bearing 2 whereas its rear end is provided with an inner threading 15 in which a stopper 16, able to slide on the shaft 6, is screwed. A spring 17 compressed between the stopper 16 and a shoulder 18 of the shaft 6 ensures closing of the clamping chuck. The clamping sleeve 9 is made solid for rotation with the central shaft 6 by friction of the pincers 14 and by the action of the spring 17.

The body 1 has three windows 19 equi-spaced about its periphery and at the same distance from the end. The windows 19 coincide with three corresponding windows 20 with inclined walls formed on a sleeve of tempered steel 21 fixed in the body 1 and serving to reinforce the walls of the windows 19 of the body to avoid wear to them. A steel ball 22 is placed on each of the three windows 19/20. These three balls 22 are held spaced apart from the shaft 6 by a spring 23 (FIG. 1a) formed by a collar 23' which fits on the body of bearing 5 and is extended longitudinally by three equidistant blades 23" with outwardly-curved ends, these blades 23" being disposed in three corresponding grooves 24 of bearing 5. The balls 22 bear externally against the conical inner wall 25 of a sleeve 26 slidably mounted on the handpiece body 1. A ring 27 lodged in an external circular groove of the body 1 serves as front stop for the sliding ring 26.

When the practioner desires to change the burr or other tool 13, he pushes the sleeve 26 towards the rear of the handpiece. By this action, the balls 22 are pushed inwards by the conical inner wall 25 of the sleeve 26. As they are pushed in against the action of the spring 23, the balls 22 bear on the rear face 28 of the windows 20 and come to occupy the position indicated in broken lines, pushing the stopper 16 and clamping sleeve 9 forward against the action of spring 17. As a result, there is a relaxation of the clamping chuck and the tool 13 can be removed, the chuck remaining in this open or tool-releasing position when a forward cylindrical part of the inner surface of the sleeve 26 comes to bear on the balls 22.

To fix a new tool in the clamping chuck, it suffices to insert the tool and move the sleeve 26 back to its initial position of FIG. 1, the balls 22 under the action of the spring blades 23" reassuming their initial position thus removing the pressure exerted on the stopper 16 and clamping sleeve 9 which are moved by the spring 17 to once more provide clamping of the chuck.

As shown, the rear face of the stopper 16 is provided on its external edge with a chamfer 29 which facilitates the action of the thrust exerted by the balls 22 and avoids an over-great wear.

Figure 3:
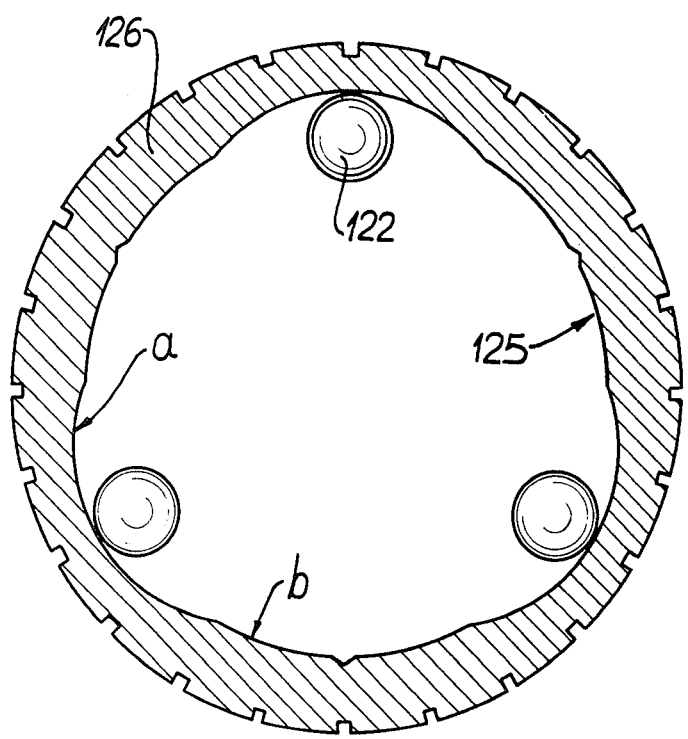
FIG. 3 is a cross-section along line III—III of FIG. 2, but showing only the balls and their external actuating sleeve.

The contra-angle handpiece shown in FIGS. 2 and 3 comprises a principal body 101 having at its front end a bearing 102 and at its rear end a threading 103 into which is screwed a rear part 104 of the contra-angle. In a known manner, a rear part of reduced diameter of the central shaft 106 is supported in a bearing 102' whereas on its front part is slidably mounted a clamping sleeve 109. The chuck for clamping a tool 113 is formed by pincers 114 having conical end faces compressed between a stop member 113 force-fitted in the bored forward end of the shaft 106 and a conical face 110 of the clamping sleeve 109.

On the rear end of the clamping sleeve 109 is screwed a stopper 116 sliding on the shaft 106, a spring 117 compressed between the stopper 116 and a shoulder 118 of the shaft 106 biasing the sleeve 109 to provide closure of the chuck. The body 101 has three windows 119 equidistantly spaced about its periphery at the same distance from the end, these windows coinciding with an inner housing limited by a conical face 129 of the stopper 116 and the chamfered end of a ring 121 fixed in the body 101.

A steel ball 122 is placed in front of each of these three windows 119. In the normal closed or tool-gripping position of the chuck, the balls 122 are held spaced apart from the shaft 106 and from the stopper 116 by a biasing spring 123. This spring 123 is formed by three axially extending equidistant blades having outwardly bent ends which lead into the openings 119 and contact the balls 122. The spring blades which are lodged in grooves 124 of a ring 105, are united by a collar fixed in the ring 105. The balls 122 are pushed by the spring 123 against the inner face 125 of a sleeve 126 rotatably mounted on the handpiece body 101 between two axial stops, namely a ring 127 and a shoulder 101' of body 101. The inner face 125 of the rotary sleeve 126 has three cam-surfaces each corresponding to a ball 122, each of these surfaces comprising a zone $a$ removed from the centre and a zone $b$ close to the centre.

When, as shown in FIG. 3, the balls 122 are located centrally in the zone $a$ under the action of the biasing spring 123, they are spaced apart from the central shaft 106; this corresponds to the closed position of the clamping chuck. Starting from the closed position, by turning the sleeve 126 by 1/6th of a turn in either direction, the zones $b$ of the inner wall 125 are brought facing the balls 122 which are radially pushed in the openings 119 of the body 101 against the action of the spring 123. In this position, the balls 122 bear against the conical face 129 of the stopper 116, and the clamping sleeve 109 is moved against the action of spring 117 to open the chuck. Hence, a rotation by 1/6th of a turn of the sleeve 126 in either direction enables actuation of the clamping chuck. The chuck can be held in the open position by engagement of the balls 122 in shallow central recesses in the zones $b$.

In both embodiments, during operation there is no contact between the rotary parts of the handpiece and the balls and the external actuating sleeves 26, 126.

What is claimed is:

1. In a dental handpiece comprising a hollow body, a central rotary shaft rotatably mounted in the body, a tool-gripping chuck carried by a forward end of the shaft, a first chuck-actuating sleeve slidably axially mounted on the shaft between a first position corresponding to a tool-gripping position of the chuck and a second position corresponding to a tool-release position of the chuck, a first spring biasing the tool-gripping sleeve axially relative to the shaft, said sleeve having a generally conical wall, at least one radially-movable ball cooperating with said generally conical wall of the first sleeve, and an external second chuck-actuating sleeve on the body cooperating with the ball to radially inwardly move the ball to axially move the first sleeve against the action of the biasing spring, the improvement wherein said at least one ball is disposed in an opening of the body, a second spring biasing said ball radially outwardly to a rest position against an inner wall of the second sleeve and out of contact with said conical wall of the first sleeve, in which rest position of the ball the first sleeve is biased by the first biasing spring to said first position, the second sleeve being manually movable and having on its inner wall an inclined part which moves the ball radially inwardly against the action of the second spring through said opening into contact with said conical wall of the first sleeve to move the first sleeve to its second position in response to movement of the second sleeve.

2. A handpiece according to claim 1, comprising three balls disposed in three discrete openings spaced about the periphery of the body.

3. A handpiece according to claim 1, in which the body comprises a ring of tempered steel having, coincident with each said opening of the body, an opening with inclined walls against which a ball bears.

4. A handpiece according to claim 1, in which said generally conical wall of the first sleeve is formed by a chamfered edge of a stopper screwed to a rear end of the first sleeve.

5. A handpiece according to claim 1, in which the chuck comprises gripping pincers with conical ends compressed between a conical stop on the shaft and a conical face of the second sleeve.

6. A handpiece according to claim 2, in which second biasing spring comprises three equidistant spring blades disposed parallel to the shaft and extending from a ring mounted in the handpiece body to outwardly bent ends disposed under the balls.

7. A handpiece according to claim 1, in which the second sleeve is axially slidably mounted on the body, said inclined part of its inner wall being conical.

8. A handpiece according to claim 1, in which the second sleeve is rotatably mounted on the body, the inner wall of the second sleeve having, for each ball, a cam surface cooperating with the ball to move it radially inwards when the second sleeve is rotated in either direction from a rest position.

9. A handpiece according to claim 8, comprising three balls disposed in three discrete openings spaced about the periphery of the body, each ball having a second biasing spring, said inner wall of the second sleeve having three corresponding cam surfaces whereby said balls are moved radially inwardly to move the first sleeve to its second position in response to turning of the second sleeve by 1/6th of a turn in either direction.

* * * * *